United States Patent [19]

Sperner et al.

[11] 4,358,271

[45] Nov. 9, 1982

[54] METHOD OF PREPARING CERAMIC-COATED DENTAL PROSTHETIC CONSTRUCTIONS

[75] Inventors: Franz Sperner, Hanau, Fed. Rep. of Germany; Heidi Brink, deceased, late of Gründau, Fed. Rep. of Germany, by Rainer Brink, heir

[73] Assignee: Heraeus Edelmetalle GmbH, Hanau am Main, Fed. Rep. of Germany

[21] Appl. No.: 233,409

[22] Filed: Feb. 11, 1981

[30] Foreign Application Priority Data

Mar. 6, 1980 [DE] Fed. Rep. of Germany ....... 3008605

[51] Int. Cl.³ ............................................... A61K 6/08
[52] U.S. Cl. .................................... 433/201; 433/206; 433/207; 433/208; 433/223
[58] Field of Search ............... 433/199, 200, 201, 202, 433/206, 207, 208, 212, 223

[56] References Cited

U.S. PATENT DOCUMENTS

| | | | |
|---|---|---|---|
| 1,892,490 | 12/1932 | Hejcmann | 433/207 |
| 3,052,982 | 9/1962 | Weinstein | 433/206 |
| 3,667,936 | 6/1972 | Katz | 75/134 N |
| 3,928,913 | 12/1975 | Schaffer | 433/207 |
| 3,981,723 | 9/1976 | Tuccillo | 433/207 |
| 4,125,442 | 11/1978 | Rogers | 204/38 C |
| 4,129,944 | 12/1978 | Sung et al. | 32/8 |

*Primary Examiner*—Lorenzo B. Hayes
*Attorney, Agent, or Firm*—Sprung, Horn, Kramer & Woods

[57] ABSTRACT

An improved method for preparing a dental prosthetic construction such as a crown or bridge is described by applying a dental ceramic composition to a base of a precious metal silver-containing alloy, drying it and firing the same. In accordance with the improvement, the firing is conducted in a reducing atmosphere.

1 Claim, No Drawings

METHOD OF PREPARING CERAMIC-COATED DENTAL PROSTHETIC CONSTRUCTIONS

BACKGROUND OF THE INVENTION

1. Field of the Invention

This invention relates to a method of preparing a dental prosthetic construction, and particularly a crown or bridge, of ceramic fired to precious metal alloys containing silver.

2. Discussion of Prior Art

Dental prosthetic constructions made of ceramic fired to metallic materials, also known as composite metal/ceramic dental reconstructions, are prepared by firing dental ceramic compositions onto appropriately configured metal structures. To this end, the ceramic compositions, which consist mainly of an opaque base composition, a color-bearing dentin composition and a transparent incisal composition, are applied in the form of usually aqueous slurries in successive layers to structures cast from alloys which either contain precious metals or are free of them, dried, and fired. The firing temperature ranges from about 900° to 1000° C.

Firing of the dental ceramic compositions is usually done in vacuum furnaces in whose firing chambers a reduced pressure with a residual atmospheric-oxygen content can be established.

Apart from silver-free precious-metal alloys on a gold basis, less costly alloys containing palladium, silver, and less gold than gold-based alloys, or no gold at all, are being used increasingly in the field of dentistry.

When silver-containing precious-metal alloys are used as baking alloys, the ceramic facings sometimes exhibit undesirable yellowing after firing.

SUMMARY OF THE INVENTION

The invention thus has as its object to provide a method of preparing dental prosthetic constructions, and particularly crowns and bridges of ceramic fired to precious metal alloys containing silver by applying dental ceramic compositions to the alloys, drying them, and firing them, which results in ceramic facings that are free of undesired coloration.

In accordance with the invention, this object is accomplished by firing the dental ceramic compositions in a reducing atmosphere.

Dental ceramic compositions are all ceramic materials which are used to create dental prosthesis looking as natural as possible. They are, in the main, opaque base compositions, color-bearing dentin compositions and transparent incisal compositions.

It has been found advantageous to employ a reducing atmosphere of or containing carbon monoxide.

It has proved particularly advantageous to produce the reducing atmosphere in the firing chamber of the furnace from atmospheric oxygen and carbon. Graphite or carbon placed in the firing chamber then serves as source of the carbon.

In lieu thereof, a reducing atmosphere producing agent may be added to the dental ceramic compositions.

The method in accordance with the invention makes it possible to produce in conventional furnaces for dental ceramics in a simple way discoloration-free ceramic facings on baking alloys of precious metals containing silver by the use of commercially available dental ceramic compositions. In particular, the method permits ceramic-coated crowns and bridges to be obtained in light tooth colors.

In the example which follows, the preparation in accordance with the method of the invention of a composite metal/ceramic dental prosthesis construction in the form of a bridge by the use of Vita VMK68 Al(trade name) dental ceramic compositions for light tooth colors is described.

EXAMPLE

Onto a structure cast from the baking alloy Herabond N (trade name), which contains silver and palladium, and then finished, there is applied, after oxidation firing, the opaque base composition, which had been stirred into a slurry. The structure coated with the base composition is then placed on a support, on which a piece of graphite has also been placed, and dried. Then it is introduced along with the support and the piece of graphite into a vacuum furnace, whose firing chamber is heated to the firing temperature at a reduced pressure (residual atmospheric-oxygen content), and fired at 960° C. for about two minutes under reduced pressure, and for densification of the ceramic material for about another minute at normal pressure. After the structure coated with base composition has been fired and cooled, the dentin and incisal compositions are applied to it and dried and fired much like the base composition.

Comparison of the finished bridge with the light tooth colors of the color ring furnished by the manufacturer of the dental ceramic compositions used in this example points up the color fidelity of the ceramic facings prepared by the method in accordance with the invention.

It will be appreciated that the instant specification and example are set forth by way of illustration and not of limitation, and that various changes and modifications may be made without departing from the spirit and scope of the present invention.

The graphite or carbon is placed in the firing chamber in such an amount that practically all the atmospheric oxygen present in the firing chamber may react therewith, thereby generating a reducing atmosphere.

Where the reducing atmosphere is to be provided by including an agent in the ceramic composition itself, it is preferred that that agent be anyone of the following: cellulose, a derivative thereof, especially starch, and terpineol.

Generally speaking, said agent included in the ceramic composition is present therein in an amount sufficient to provide a reducing atmosphere by reacting after thermal decomposition with the atmospheric oxygen present in the firing chamber.

The firing itself is usually effected for a period of at least 2 minutes, preferably between 3 and 5 minutes. The duration of the firing depends on the composition of the ceramic material applied. However, the firing times can be those heretofore utilized for the firing of ceramic compositions in the manufacture of a dental prosthetic construction such as a crown or bridge.

What is claimed is:

1. In the method of preparing a dental prosthetic construction, including a crown or bridge, by applying a dental ceramic composition to a precious-metal alloy-containing silver, drying it, and firing the same, the improvement wherein the firing is carried out in a reducing atmosphere comprising carbon monoxide which is produced in the firing chamber of the furnace from atmospheric oxygen and placed in the firing chamber.

* * * * *